United States Patent
Dellanno

(10) Patent No.: US 8,038,635 B2
(45) Date of Patent: Oct. 18, 2011

(54) FORWARD HEAD POSTURE CORRECTION COLLAR

(75) Inventor: Ronald P. Dellanno, Bloomfield, NJ (US)

(73) Assignees: Ronald P. Dellanno, Boonton Township, NJ (US); Gerard Malanga, Chatham, NJ (US); Michael Dellanno, West Caldwell, NJ (US)

( * ) Notice: Subject to any disclaimer, the term of this patent is extended or adjusted under 35 U.S.C. 154(b) by 111 days.

(21) Appl. No.: 12/316,805

(22) Filed: Dec. 16, 2008

(65) Prior Publication Data
US 2009/0149788 A1 Jun. 11, 2009

Related U.S. Application Data

(63) Continuation-in-part of application No. 11/172,453, filed on Jun. 30, 2005, now abandoned.

(60) Provisional application No. 60/638,061, filed on Dec. 21, 2004.

(51) Int. Cl.
*A61F 5/24* (2006.01)
*A61F 5/00* (2006.01)
*A61B 19/00* (2006.01)

(52) U.S. Cl. .................. 602/18; 602/5; 602/12; 602/17; 602/19; 602/33; 602/36; 128/97.1; 128/869; 606/237; 606/241

(58) Field of Classification Search ................ 602/5, 12, 602/17–19, 23, 33–36; 128/97.1, 848, 869; 128/DIG. 23; 606/54, 57–61, 237, 241
See application file for complete search history.

(56) References Cited

U.S. PATENT DOCUMENTS

| | | | | |
|---|---|---|---|---|
| 3,306,284 A | * | 2/1967 | Mckinley | 602/18 |
| 3,601,123 A | * | 8/1971 | McFarland | 602/18 |
| 3,776,224 A | * | 12/1973 | McFarland | 602/18 |
| 4,793,334 A | * | 12/1988 | McGuinness et al. | 602/18 |
| 5,302,170 A | * | 4/1994 | Tweardy | 602/17 |
| 5,752,927 A | * | 5/1998 | Rogachevsky | 602/18 |
| 6,267,741 B1 | * | 7/2001 | Lerman | 602/18 |
| 6,503,213 B2 | * | 1/2003 | Bonutti | 602/5 |
| 6,770,047 B2 | * | 8/2004 | Bonutti | 602/18 |

* cited by examiner

*Primary Examiner* — Patricia Bianco
*Assistant Examiner* — Brandon Jackson
(74) *Attorney, Agent, or Firm* — Klauber & Jackson LLC

(57) ABSTRACT

A forward head position correction collar is provided which in combination includes a shoulder collar assembly, a chin mastoid piece for engaging and positioning the head of a wearer of the collar; and interconnecting means for interconnecting the chin piece to the collar assembly as to enable the chin piece to be manually and preferably incrementally adjustable with respect to the shoulder collar assembly in a Z-direction to thereby adjust the supported head of the wearer from the forward head position to an increasingly corrected position. The interconnecting means is further adapted for displacing the chin-mastoid piece in a vertical direction with respect to the shoulder collar assembly simultaneously with and proportional to the incremental adjustment of the chin-mastoid piece along the Z-axis. The proportional vertical displacement with respect to the z axis displacement for the chin-mastoid support piece is that yielded by a point moving at about a 5 to 25 degree slope with respect to the horizontal Z-axis. The correction collar may further include a lordosis correction assembly secured to the rear of the collar and engageable with the rear of the wearer for applying corrective forces to at least one or more of the cervical vertebrae of the wearer.

12 Claims, 18 Drawing Sheets

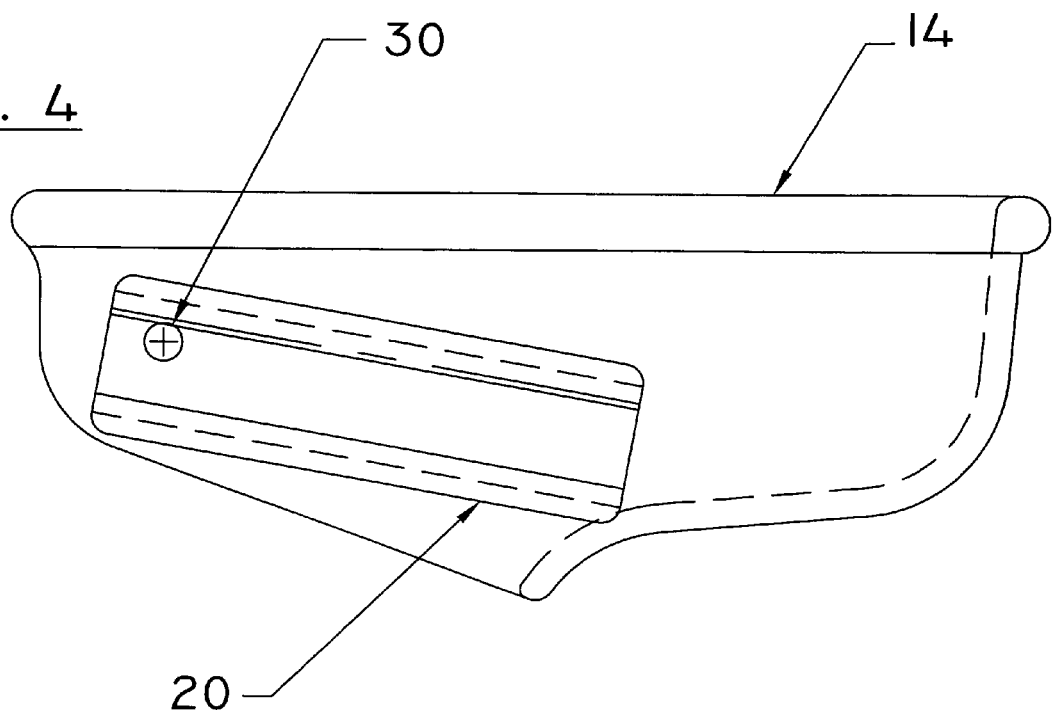

ANCHORED TO 12

(NOTE: CHIN PIECE SUPPORT BRACKET (18) SHOWN AT 0° FOR CLARITY)

(NOTE: TRACKING MECHANISM SHOWN AT 0° FOR CLARITY)

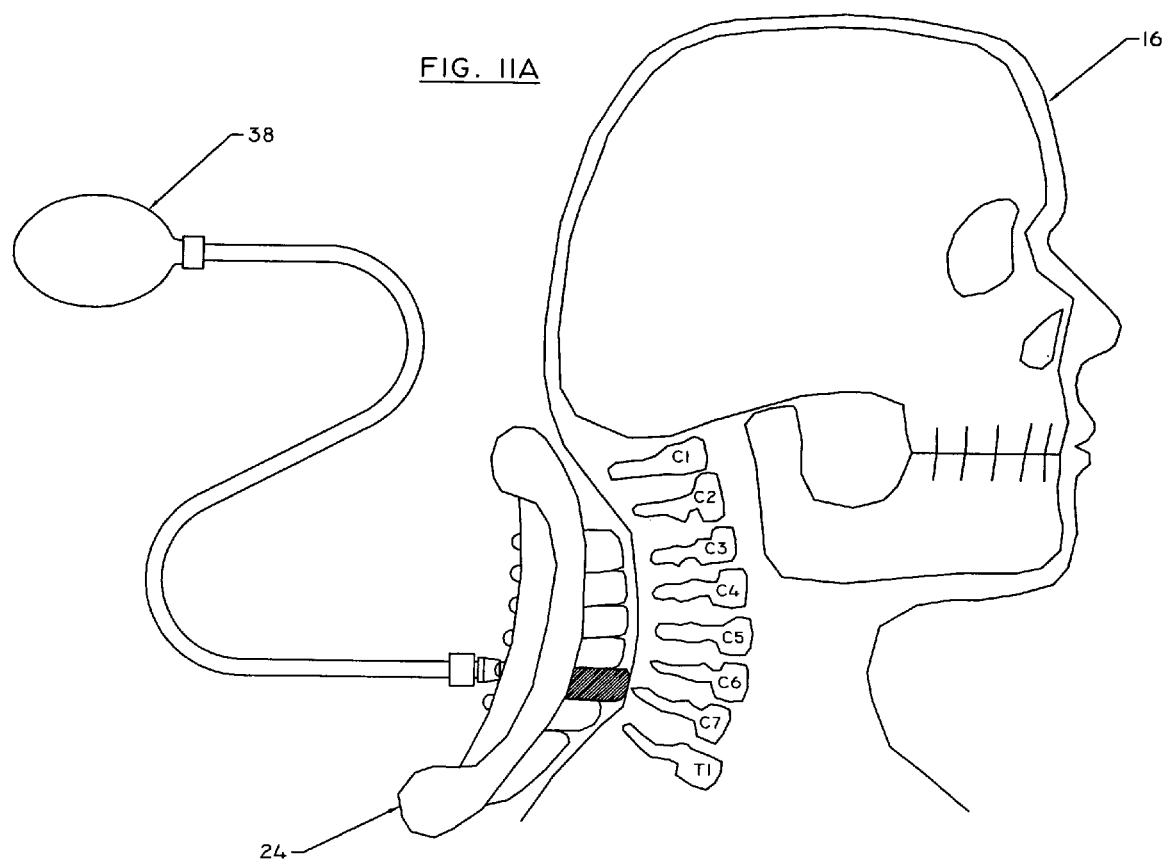

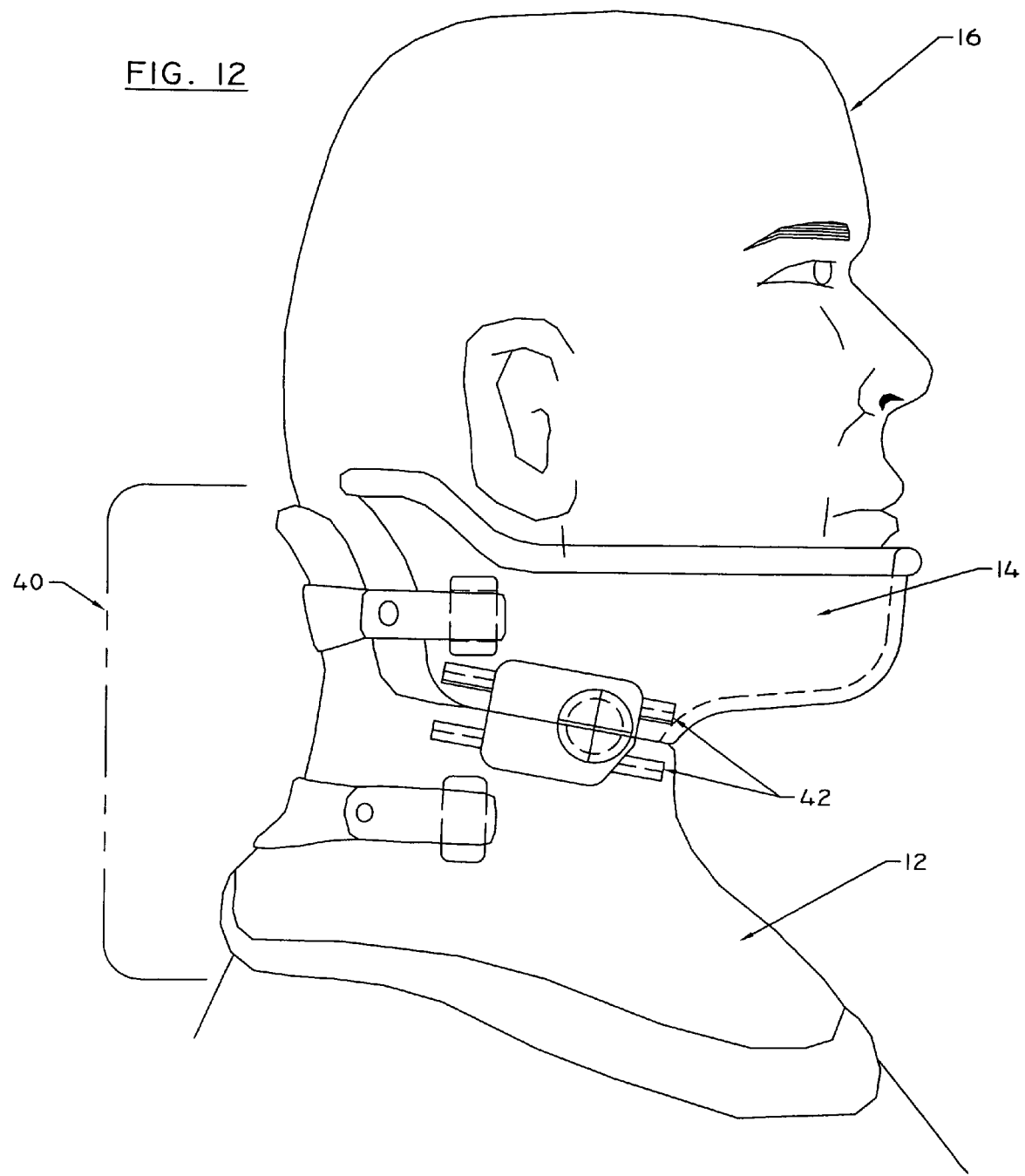

FORWARD HEAD POSTURE CORRECTION COLLAR

RELATED APPLICATIONS

This application is a continuation-in-part of U.S. application Ser. No. 11/172,453, filed Jun. 30, 2005 now abandoned; and claims priority from U.S. provisional patent application Ser. No. 60/638,061 filed Dec. 21, 2004.

FIELD OF THE INVENTION

This invention relates generally to orthopedic correction devices and apparatus, and more specifically relates to a forward head position correction collar.

BACKGROUND OF THE INVENTION

Forward head positioning is an increasingly observed malady in our society. As is well known to orthopedists, chiropractors and other medical practitioners the human head in its normal position should sit in a direct fashion on the neck and shoulders. Partly because of certain increasing habits in our society the head can become displaced to a posture where instead of sitting directly on the neck and shoulders, is displaced forward of that normal position to what is called a "forward head posture" (or "FHP"). FHP has indeed become so widespread that it may already constitute a health hazard having the ramifications of a pandemic, since when left untreated FHP can develop degenerative and disabling joint diseases affecting countless numbers of people.

There are numerous reasons why FHP is becoming such a more common problem. For example, vastly increased use of computer screens accustoms the operator to move and maintain the head in the undesirable forward head posture. The problem is also exacerbated in children and young adults by long hours devoted to video games, not to mention conventional television watching. Yet another source believed to be responsible for the malady particularly in children, is the present custom of children carrying extremely heavy backpacks to and from school. The weight of such backpacks is so high as to require head placement in a forward position to balance the load, which results in the increasing observation of forward head posture in both children and young adults.

Basic damage resulting from forward head posture (FHP) arises because the upper cervical portion of the spine can become chronically misaligned. It of course will be evident that the FHP condition need not result from undesirable habits and practices as discussed above, but can also be the result of injury.

While the difficulties arising from FHP are certainly well recognized in the healing arts, efforts to correct same by treatment with orthopedic devices and the like have not been successful. Basically such efforts have taken the form of using cervical collars to in some manner immobilize the neck. The objective of these collars, or for that matter of other prior art treatment, has simply been to utilize traction to displace the head from its improper position. Neither these prior art collars, nor to the best of applicant's knowledge any other presently available devices and/or apparatus, are however effective in reversing the damaging effects of FHP.

As used herein, the term "Z-axis" refers to the horizontal axis extending in an anterior-posterior direction with respect to a set of axis positioned at a hypothetical human, where the corresponding vertical axis is referred to as the Y-axis and the horizontal left to right side axis with respect to such human is referred to as the X-axis. Many of the prior art devices that have been used or proposed, while achieving adjustments along the Z-axis are not otherwise concerned with simultaneously improving cervical lordosis. Most cervical collars are designed to immobilize the neck and/or cause axial translation to decompress the cervical spine while causing the cervical spine straightening. This may produce mixed benefits, as ligament impairment cannot improve around a straightened cervical curve, as this is an abnormal alignment, which will ultimately result in permanent arthritic changes to the cervical joints. Ligament rehabilitation requires improvement of joint alignment over time. Most current extension traction therapy designed to improve cervical lordosis is practiced for 20 minutes or less. One objective of the present invention is to improve cervical lordosis with a full correction collar over many hours. The present invention is thus relatively comfortable and can be used at work or at home or even during sleeping hours to avoid unhealthy postures that impair the health of an injured neck.

SUMMARY OF THE INVENTION

The present invention is a new type of forward head position (FHP) correction collar, which utilizes a mild axial translation with significant corrective Z translation forces for the sagittal planes. The invention provides an orthopedic correction device which can be readily used by a patient suffering from FHP, which can reverse the damaging effects of compressive loading, shear, and neck moments which FHP generates at all seven cervical vertebra of the patient.

In accordance with the present invention a forward head position correction collar is provided which in combination includes a shoulder collar assembly, a chin-mastoid piece for engaging and positioning the head of a wearer of the collar; interconnecting means for interconnecting the chin-mastoid piece to the collar assembly as to enable the chin-mastoid piece to be manually and preferably incrementally adjustable with respect to the shoulder collar assembly in a Z-direction, to thereby adjust the supported head of the wearer from the forward head position to an increasingly corrected position; and the said interconnecting means further being adapted to displace the chin-mastoid piece in a vertical direction with respect to the shoulder collar assembly simultaneously with and proportional to the incremental adjustment of the chin-mastoid piece along the Z-axis. The proportional vertical displacement with respect to the z axis displacement for the chin-mastoid support piece is that yielded by a point moving at about a 5 to 25 degree slope, and preferably at a 10 to 25 degree slope with respect to the horizontal Z-axis.

The FHP correction collar may further include a lordosis correction assembly secured to the rear of the collar. This assembly is engageable with the rear of the wearer for applying corrective force to the upper, middle and/or lower cervical spine. The lordosis correction assembly can also be used to selectively support only one or only several of the seven cervical vertebrae, and thus need not support the entire neck curve. Further, the assembly may by virtue of its fit with a given patient, be able in such instances to support one or more of the upper thoracic vertebrae.

It is to be appreciated that the terms "forward" and "back" are often misused when applied to flexion and extension motion of the head. As described herein the reference coordinate system is one wherein the x-axis extends right to left in the frontal plane, the y-axis is the vertical axis, and the z-axis resides in the front to rear sagittal plane. The present invention is concerned with translational movement along the sagittal plane, i.e. in the direction of the z-axis (front to rear). This contrasts to much prior art as exemplified e.g. in such representative prior art as Bonutti U.S. Pat. No. 6,770,047, which is concerned with rotational movement around the x axis (flexion and extension or looking up or down movement). See e.g. FIGS. 4 and 5 of the Bonutti patent. The exemplary prior art Bonutti invention is designed to stretch the neck in flexion (negative x direction, see FIG. 4), or in extension (positive x axis direction, looking up, see FIG. 5 therein.) The patient can control this motion by an adjustable control knob located at their naval area, whereas in the present invention the control knob is in the neck area and causes a completely different motion. The present invention thus has a neck brace that moves forward (positive z axis) and rearward (negative z axis). There is no flexion or extension motion The object of the present invention is to correct cervical lordosis breakdown at specific areas and to correct forward head posture. The design of the invention is dictated by the intended motion objectives.

BRIEF DESCRIPTION OF DRAWINGS

The invention is diagrammatically illustrated by way of example in the drawings appended hereto, in which:

FIG. 4 is a side elevational view of the chin-mastoid piece of FIG. 3.

FIGS. 11 and 11A are side schematic views showing how use with the invention of the inflatable lordosis correction assembly acts in concert with the other features of invention to correct lordosis in the cervical and upper thoracic portions of the individual's spine;

FIG. 12 is a view similar to FIG. 1, but showing a second embodiment of the invention;

DESCRIPTION OF PREFERRED EMBODIMENTS

Figure 1:
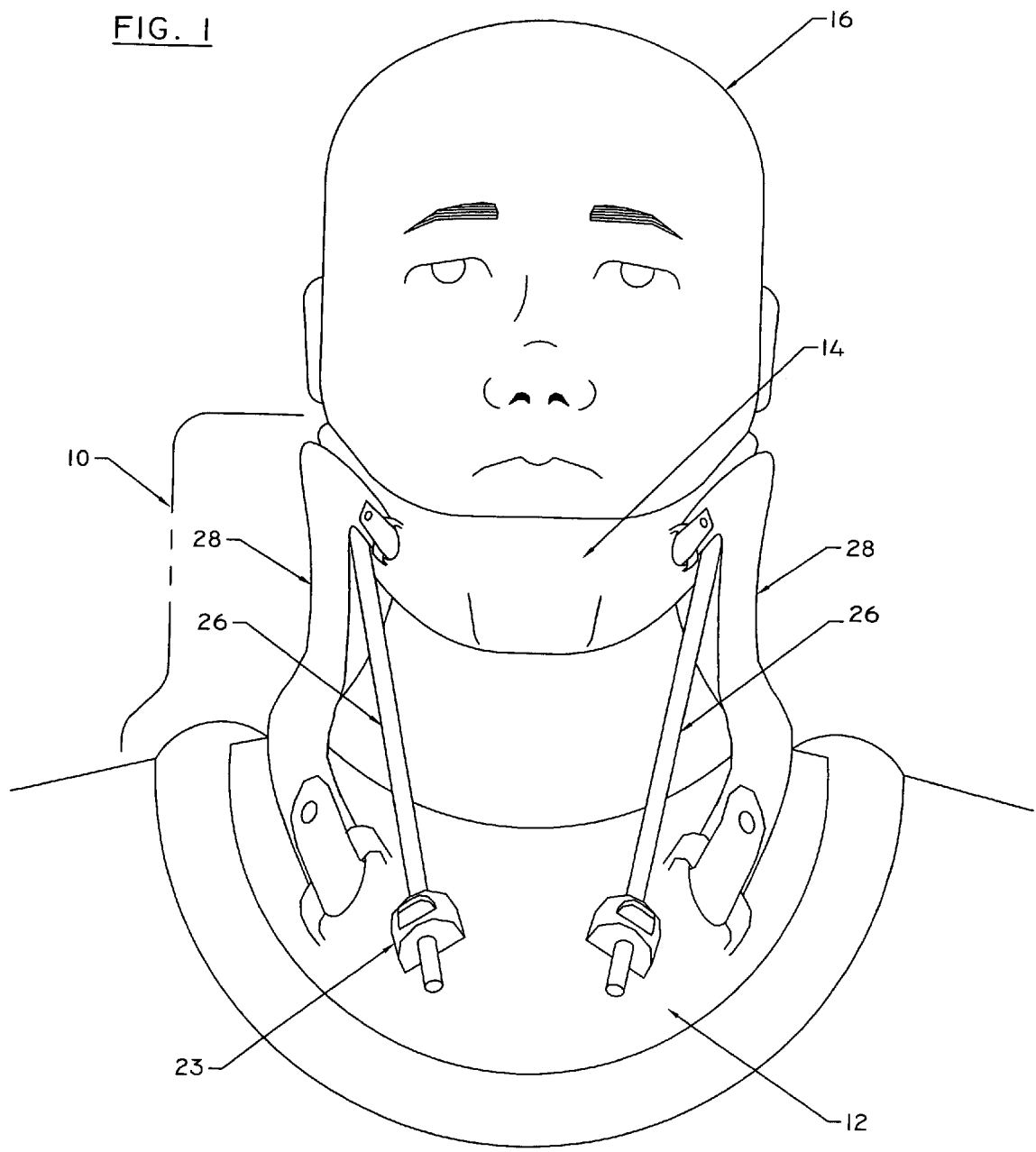
FIG. 1 is a front perspective view of a first embodiment of an FHP correction collar in accordance with the invention being utilized in connection with a representative person undergoing treatment.
Figure 2:
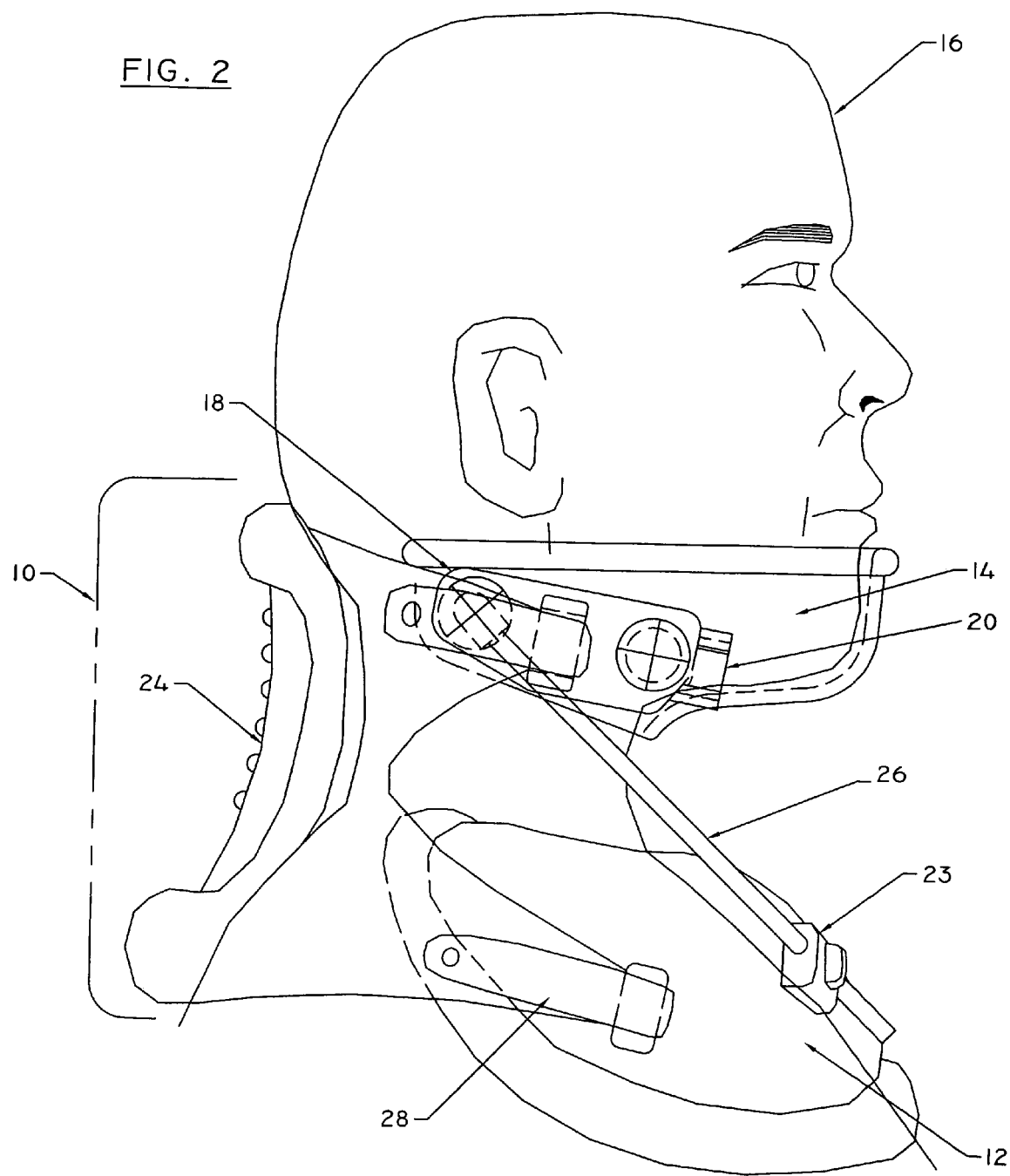
FIG. 2 is a side perspective view of the device of FIG. 1.
Figure 2A:
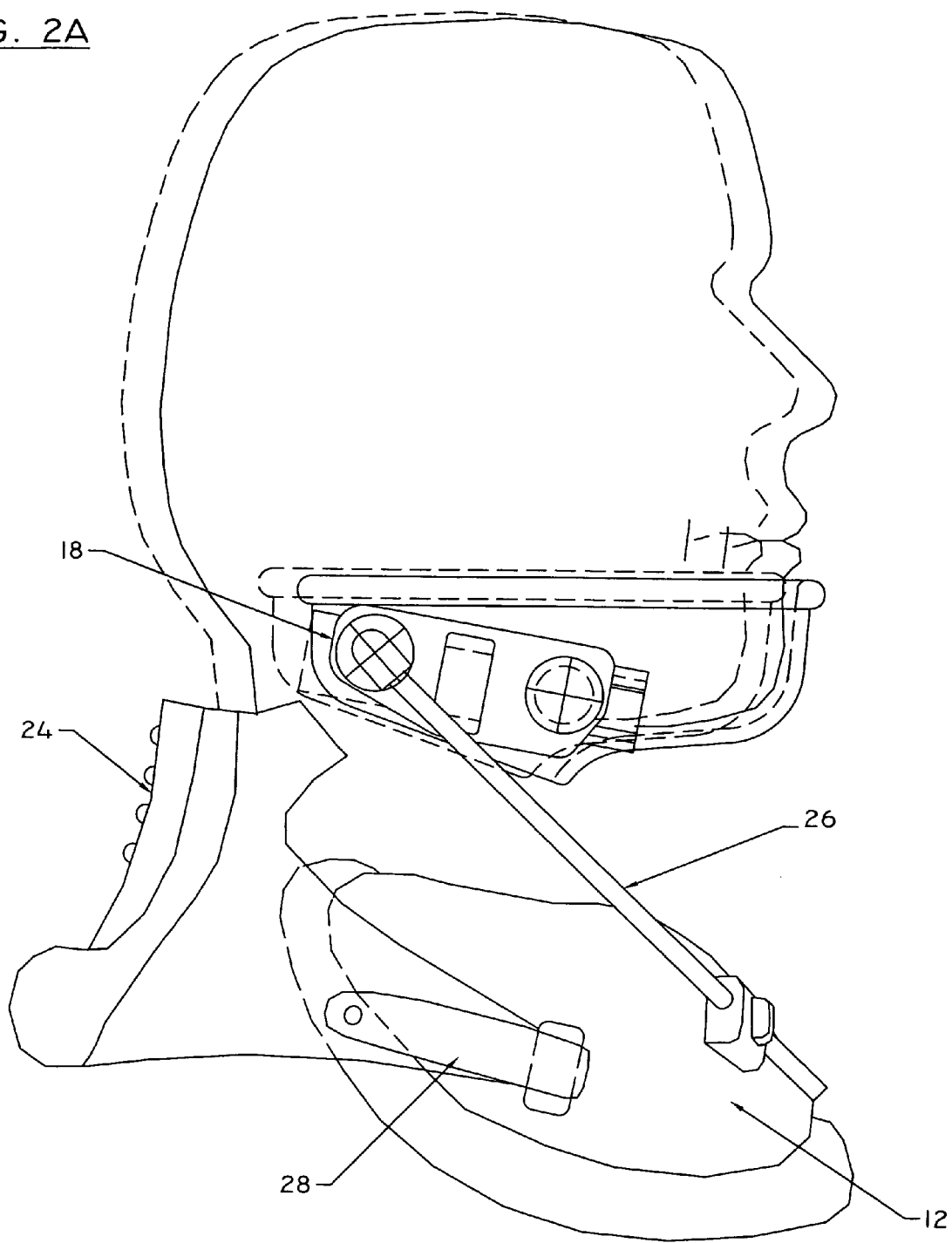
FIG. 2A is similar to FIG. 2, but shows the change in collar configuration resulting from an adjustment of the device.

In the views of FIGS. 1, 2 and 2A the forward head position correction collar 10 comprises a shoulder collar assembly 12 and a chin-mastoid piece 14, the latter being movable with respect to the former so as to adjustably reposition the head 16 of a wearer of the correction collar 10. The chin-mastoid piece 14 (FIGS. 3A, 3B, 3C and FIG. 5) is connected at each of its sides to one of a pair of chin-mastoid piece support brackets 18 (FIG. 2) by a track 20 and a rod 26. (Also as seen in FIG. 1, one such rod 26 is present at each side of collar 16). Each chin-mastoid piece support bracket 18 is connected to shoulder collar assembly 12 and to a rear lordosis correction assembly 24 (FIGS. 2 and 7) by the lower ends of connecting rods 26 and by straps 28.

Figure 10:
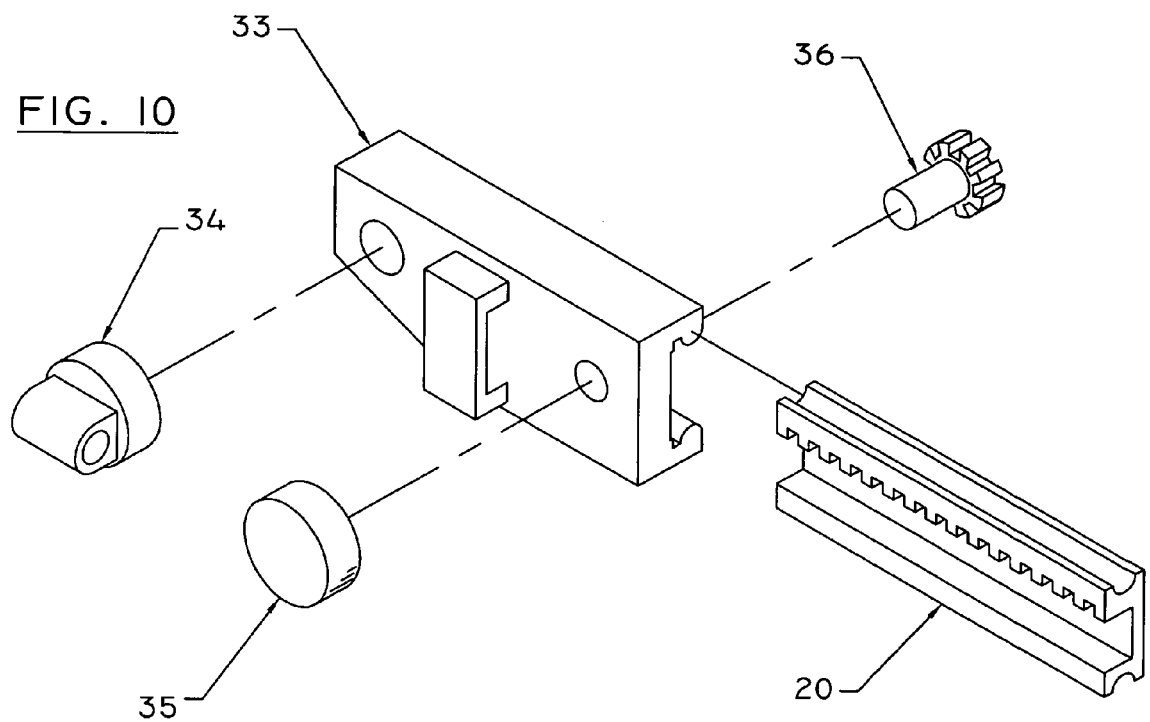
FIG. 10 is an exploded perspective view of the components shown in FIGS. 9A, 9B and 9C.

The Z-displaced and vertically displaced positions of the chin-mastoid piece 14 with respect to shoulder collar assembly 12 is adjusted by knobs 35 at each lateral side of collar 10, each of which turn a pinion gear 36 which is meshed with teeth in track 20 (FIG. 10). The rotational angle through which each knob 35 moves is preferably the same during adjustment to preserve maximum symmetry in displacement of the chin-mastoid piece. Such identity in rotation can be controlled manually or by simple interconnects. The displacement during adjustment is best seen in FIG. 2A, where the upper portion of rear bladder assembly 24 has been removed for clarity. The new positions resulting from an adjustment is shown in shadow.

Figure 3A:
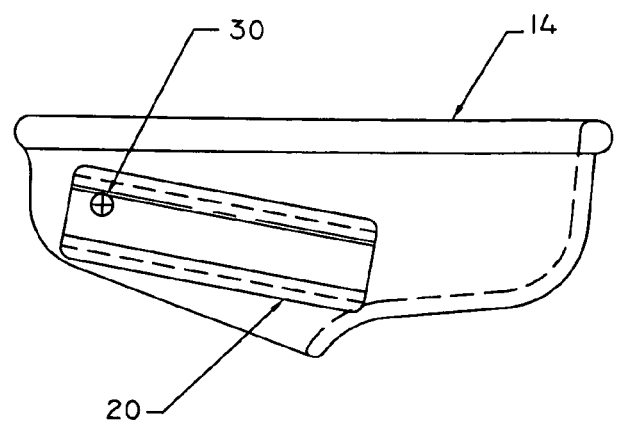
FIGS. 3A, 3B and 3C are respectively side, ¾, and top views in perspective of the chin-mastoid piece used in the FIGS. 1 and 2 embodiment.
Figure 3B:
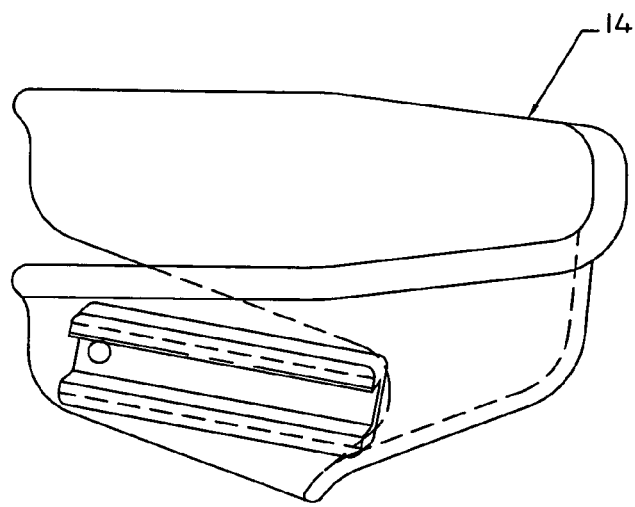
Figure 3C:
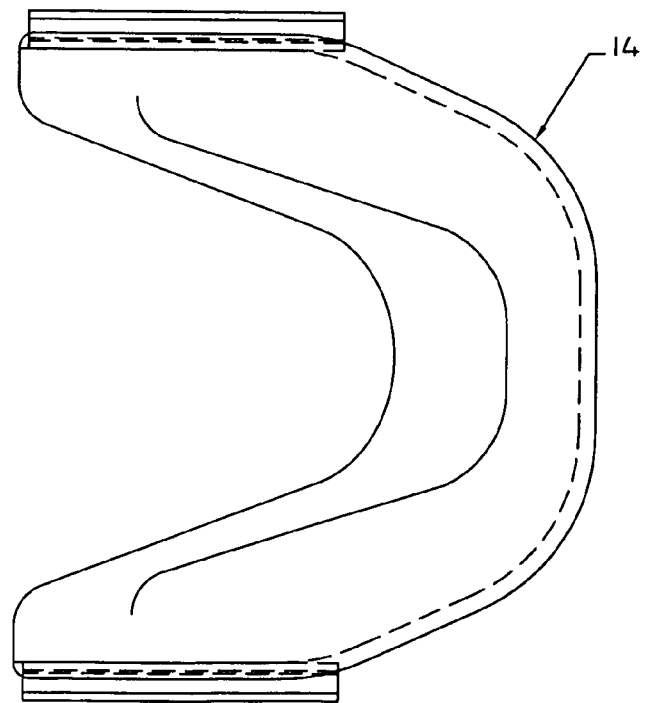
Figure 5A:
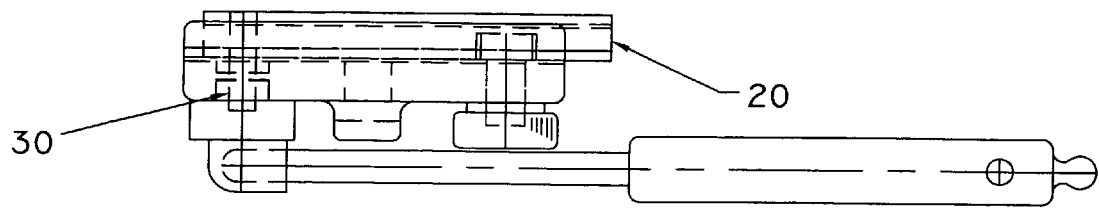
FIGS. 5A and 5B are respectively top and side views of the chin-mastoid piece support bracket and the components interacting therewith in connection with the embodiments of the prior Figures.
Figure 5B:
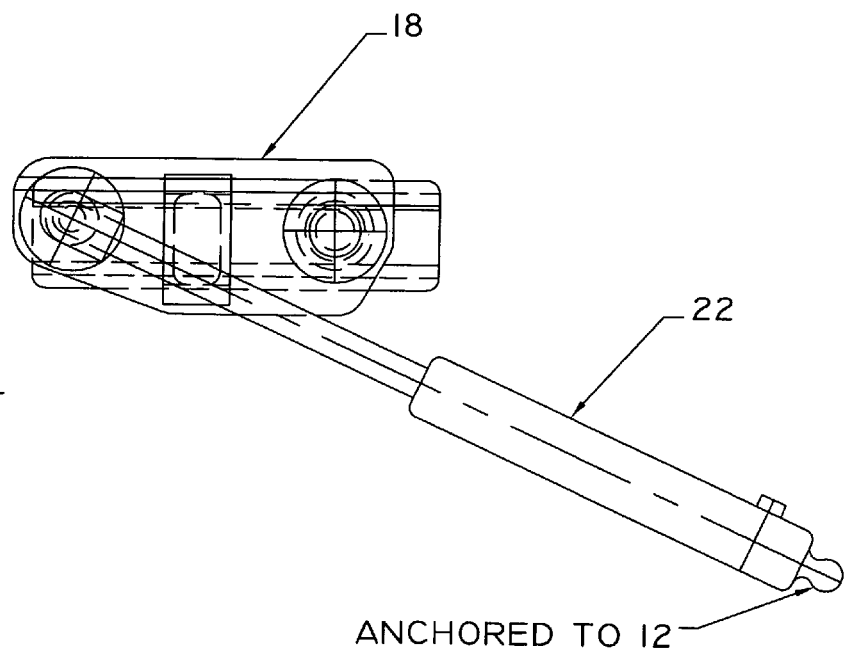

The chin-mastoid piece 14 is shown in further detail in the side, ¾, and top perspective views of FIGS. 3A, 3B and 3C.

Figure 6A:
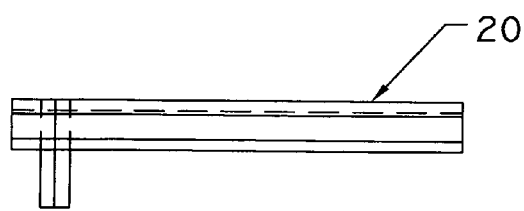
FIGS. 6A, 6B and 6C are respectively plan, top and end views of the support track portion of the showing in FIGS. 4 and 5 B.
Figure 6B:
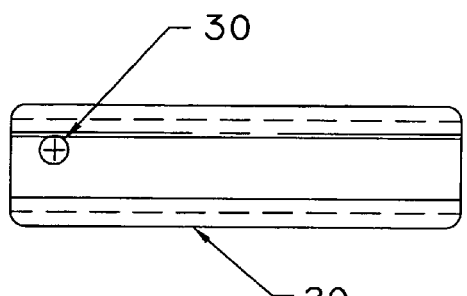
Figure 6C:
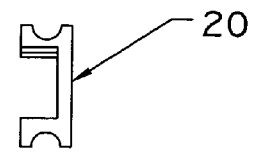

Operation of the device is better understood by reference to FIGS. 2 through 5. As seen in FIGS. 3A and 3B the chin-mastoid piece 14 is provided with a track 20 (one of a pair, the other being symmetrically secured at the opposed lateral face of piece 14). The form of track 20 may be better seen in FIG. 10. Chin-mastoid piece 14 has a chin-mastoid piece alignment pin 30 (FIG. 6B) permanently affixed to one side of the chin-mastoid piece and projecting outwardly. The chin-mastoid piece 14 is attached to chin-mastoid piece support bracket 18 via the track 20 which engage in slidable fashion with bracket body 33. The alignment pin 30 is thus seen to engage with the chin piece support bracket 18 and retained by pivot cap 34. Each of rods 26 is secured between alignment pin 30 and an anchoring point on shoulder assembly 12 (see FIGS. 5A and 5B). An air or other cylinder 22 can be associated with rods 26 to act as a dampening means during the manual adjustments.

Thus when the knob 35 is rotated, displacement upwardly of the chin-mastoid piece 14 is enabled with respect to assembly 12 because of an incline of the support track 20 as seen in FIG. 4, and of the alignment maintained in the chin piece support bracket 18. Note that in FIG. 5B the chin-mastoid support material support bracket 18 is schematically shown at 0° for purposes of clarity.

The interaction between the chin piece support bracket 18 and the chin-mastoid piece 14 is better seen in FIG. 10. When the adjustment is made the rods 26 are first released by rotating release means 23 (FIG. 1) which are locked once the adjustment is complete. The incline for the support track can be in the general range of from about 50 to about 25°, with a preferred incline range being from about 10° to about 25°) and a typical preferred incline being about 10°.

A further embodiment 40 of the invention is schematically illustrated in FIG. 12. In this embodiment just a rack and pinion arrangement is used to enable the desired displacement between the chin-mastoid piece 14 and the shoulder collar assembly 12. In this instance the track 42 is defined as to bridge bordering portions of piece 14 and shoulder assembly 12, but as in the prior embodiment the desired slope of the track with respect to the horizontal Z-axis is maintained.

Figure 8B:
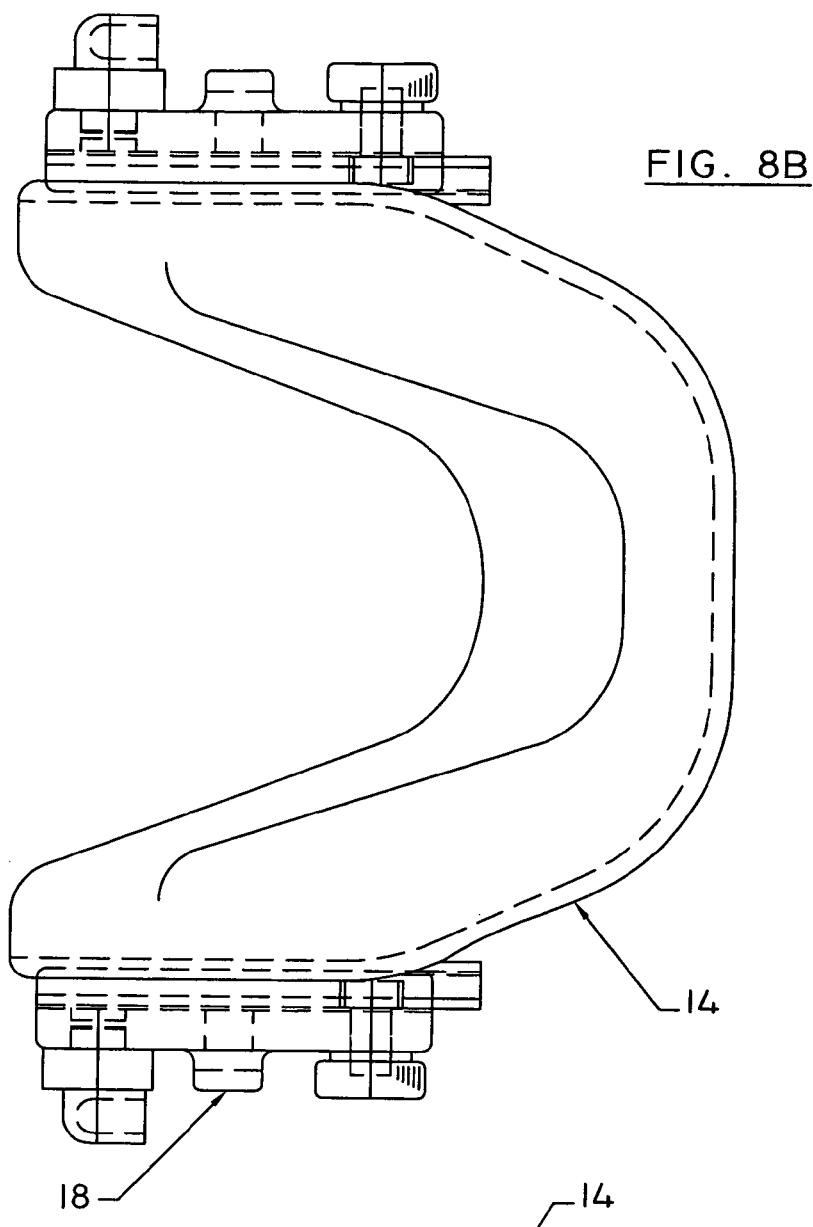
FIGS. 8A and 8B are side and top views of the chin-mastoid piece and chin-mastoid piece support bracket used in the embodiment of FIG. 7.
Figure 8A:
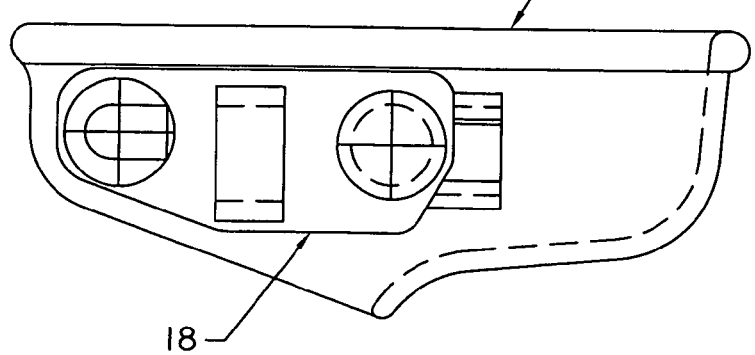
Figure 9B:
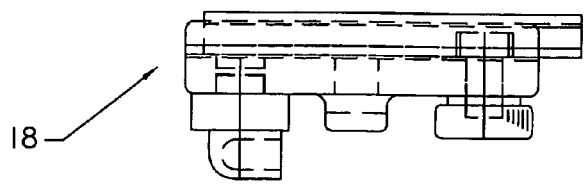
FIGS. 9A, 9B, and 9C are respectively plan, top, and end views of the chin-mastoid piece support bracket.
Figure 9A:
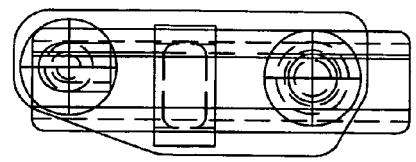
Figure 9C:
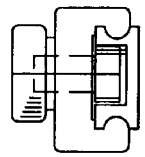

Side and top perspective views of the chin-mastoid piece 14 and associated chin-mastoid piece support bracket 18 appear in FIGS. 8A and 8 B. The mastoid bone is located behind the subject's ear and serves as an excellent lever-arm to move the head rearward in correcting the forward head posture. The mastoid bone is part of the head while the chin is part of the jaw, which is connected to the head. Engaging and using the chin alone, while workable, could possibly cause jaw problems.

Figure 7:
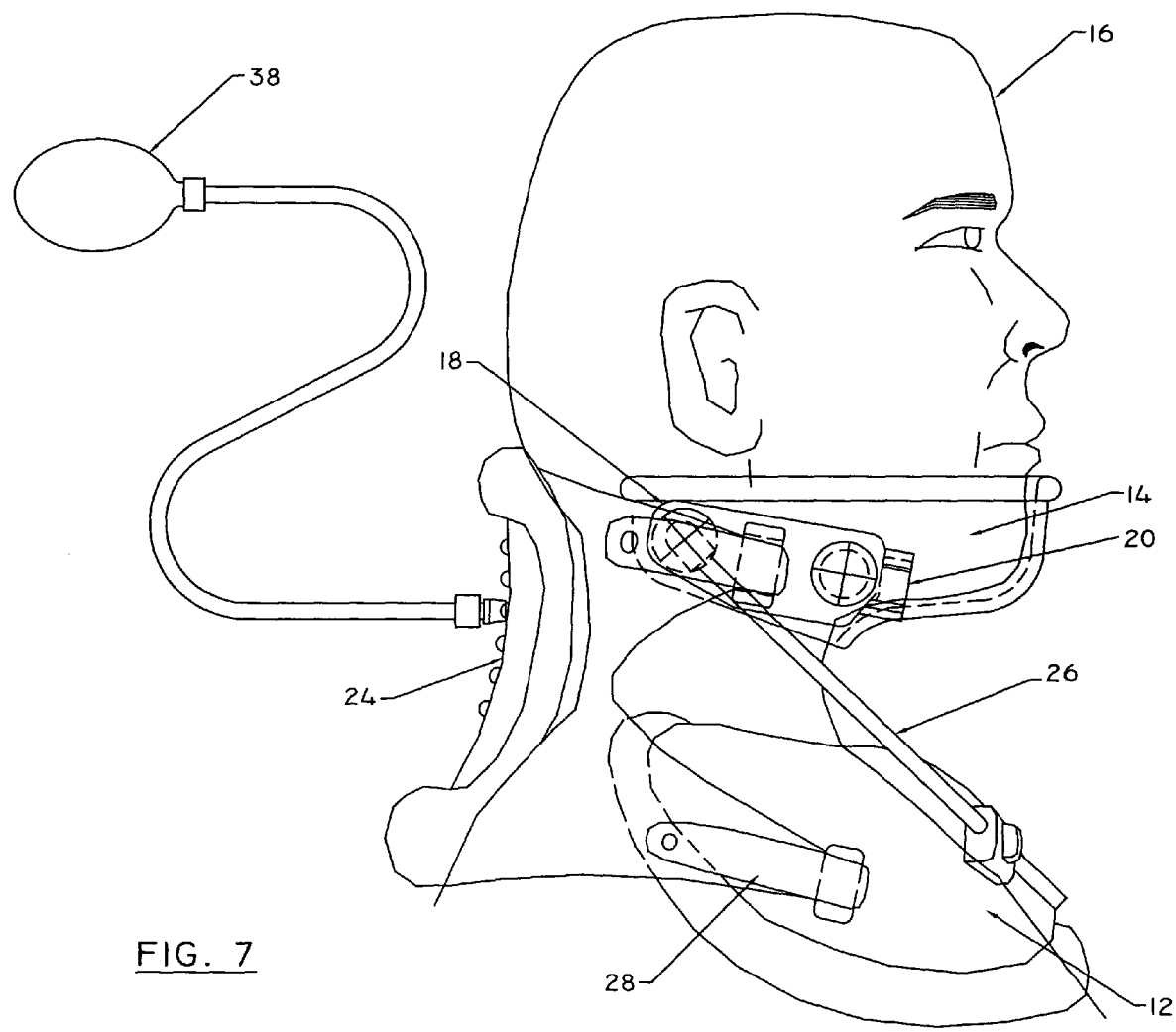
FIG. 7 is a view similar to FIG. 2, and showing further details of the inflatable lordosis correction assembly which can be used in the invention.
Figure 11:
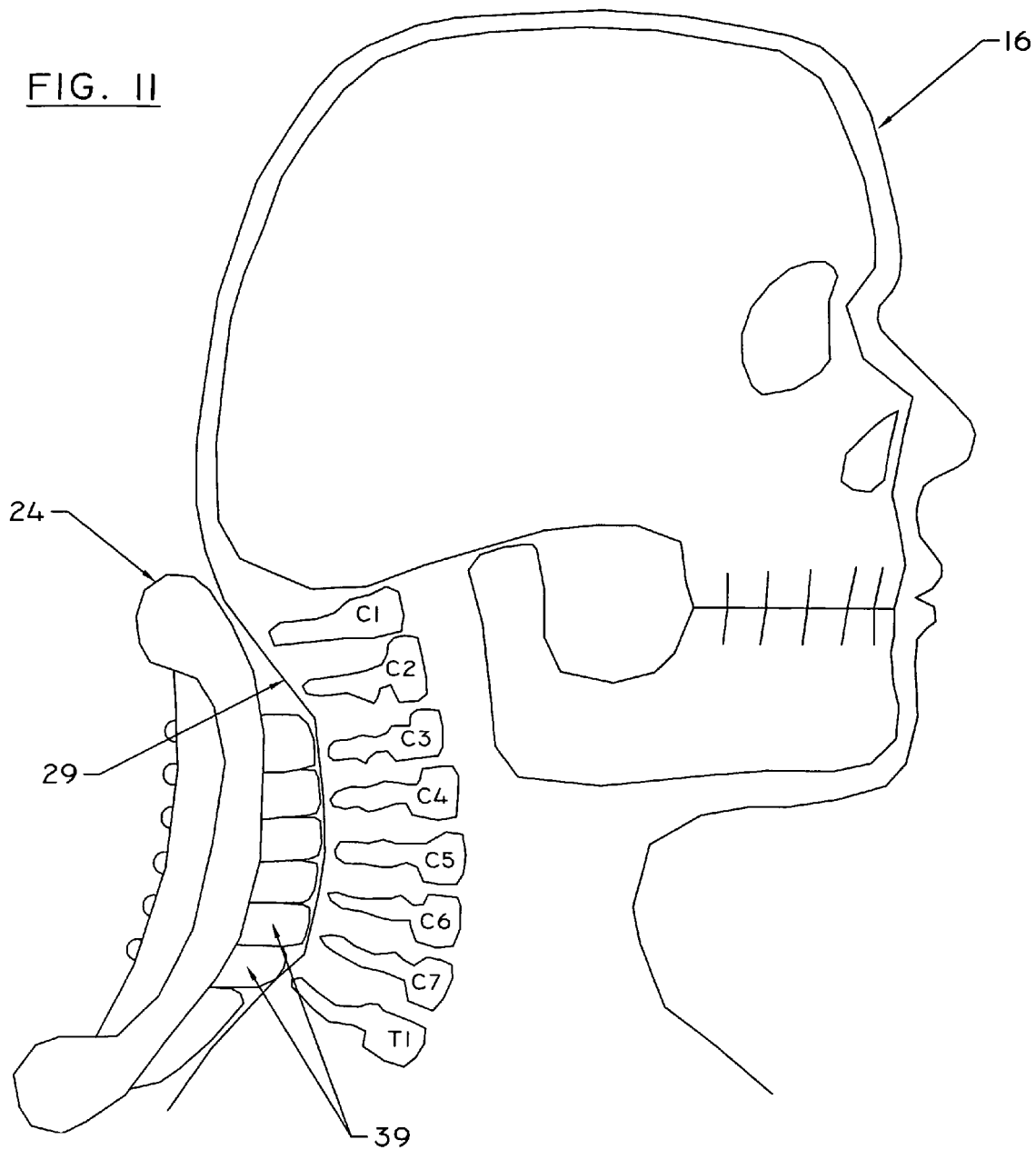
Figure 13:
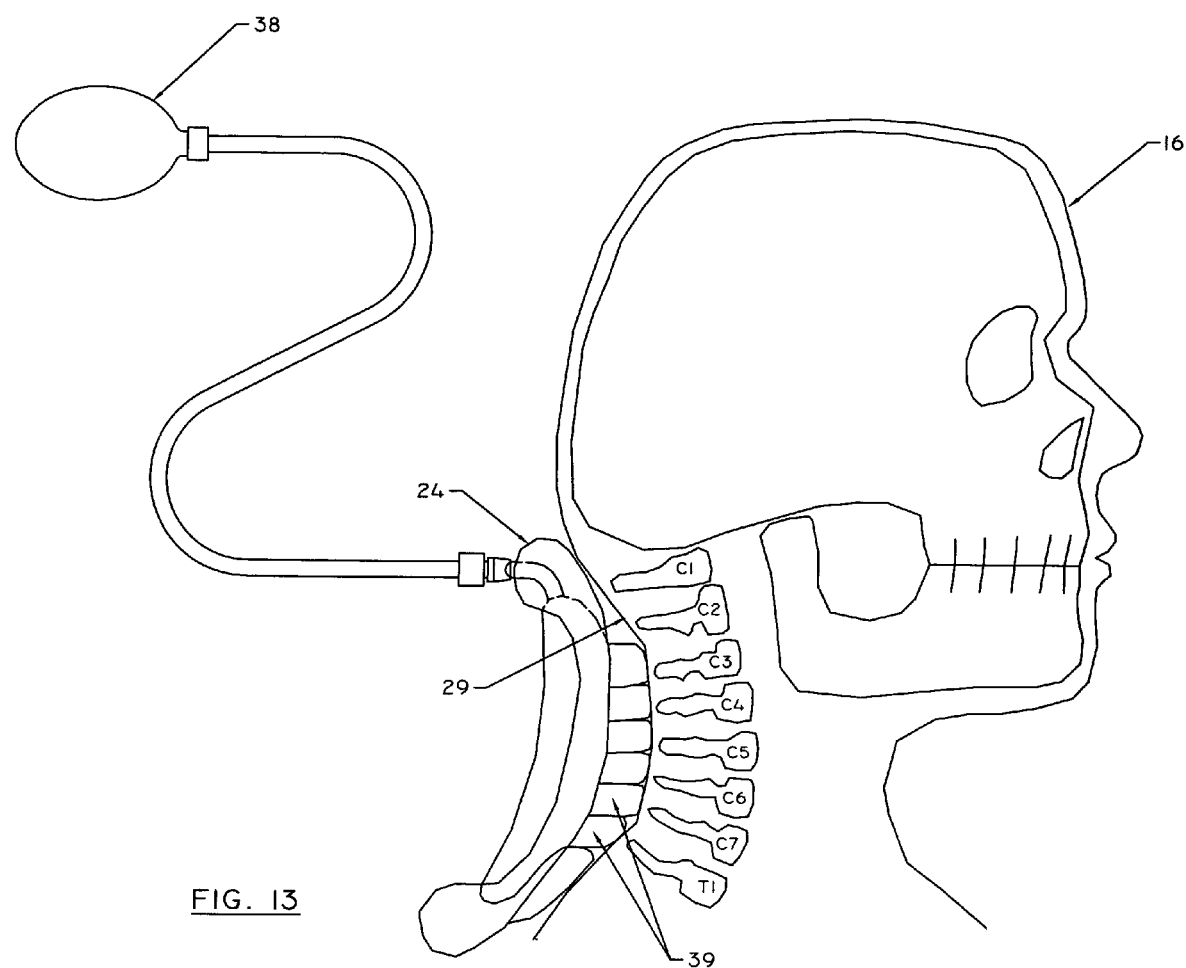
FIG. 13 is a side schematic view similar to FIGS. 11 and 11A, but showing the air bladder being filled at one position while a rigid foam lordosis pad contacts the rear portion of the patient's neck.

The present apparatus as further seen in FIGS. 7, 11 and 13 can also be associated with a lordosis correction assembly 24, which as is seen in these schematic views can comprise a user inflatable portion and an underlying pressure contact surface 29. The assembly 24 is inflatable by a simple hand bulb as shown at 38 (FIG. 13). The purpose of this assembly is to correct the lordosis curve upon the selected displaced position of the chin-mastoid piece 14 being achieved. The precise form of the lordosis correction surface 29 may be in accord with the devices and curvature configurations discussed at length in the present inventor's U.S. Pat. Nos. 5,181,763, 5,290,091 and 5,580,124, among others. Such disclosures are incorporated by reference herein.

The correction surface 29 can comprise a plurality of separate adjoining pads 39. These can be of a foam or a similar material, or as shown in FIGS. 11 and 11a can be each a separate inflatable unit or cell. This enables increased pressure to be brought selecting against specified vertebrae. Thus separate input ports such as 41, 43 etc. can be connected to an air pressure source to expand the connected inflatable unit against a particular vertebra. FIG. 11A shows such a connection being made in order to advance the expanded pad 39a against the C7 vertebra. Interconnection between input port 41 and pad 39 is made by a tube and suitable valving.

Figure 14:
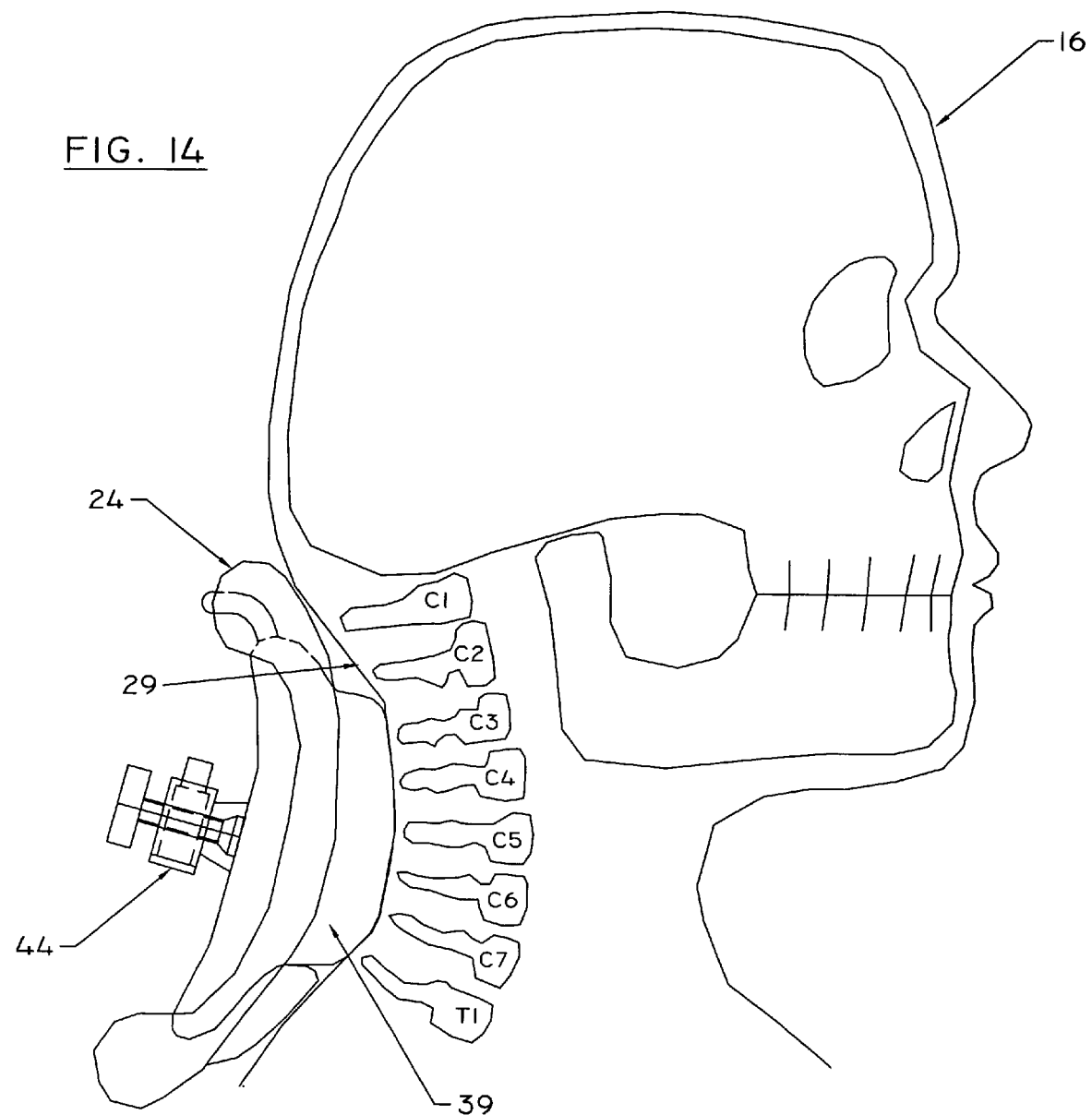
FIG. 14 is a further side schematic view showing the air bladder and lordosis pad contacting the back of neck, as a tensioning mechanism applies pressure to the back of the neck.
Figure 15:
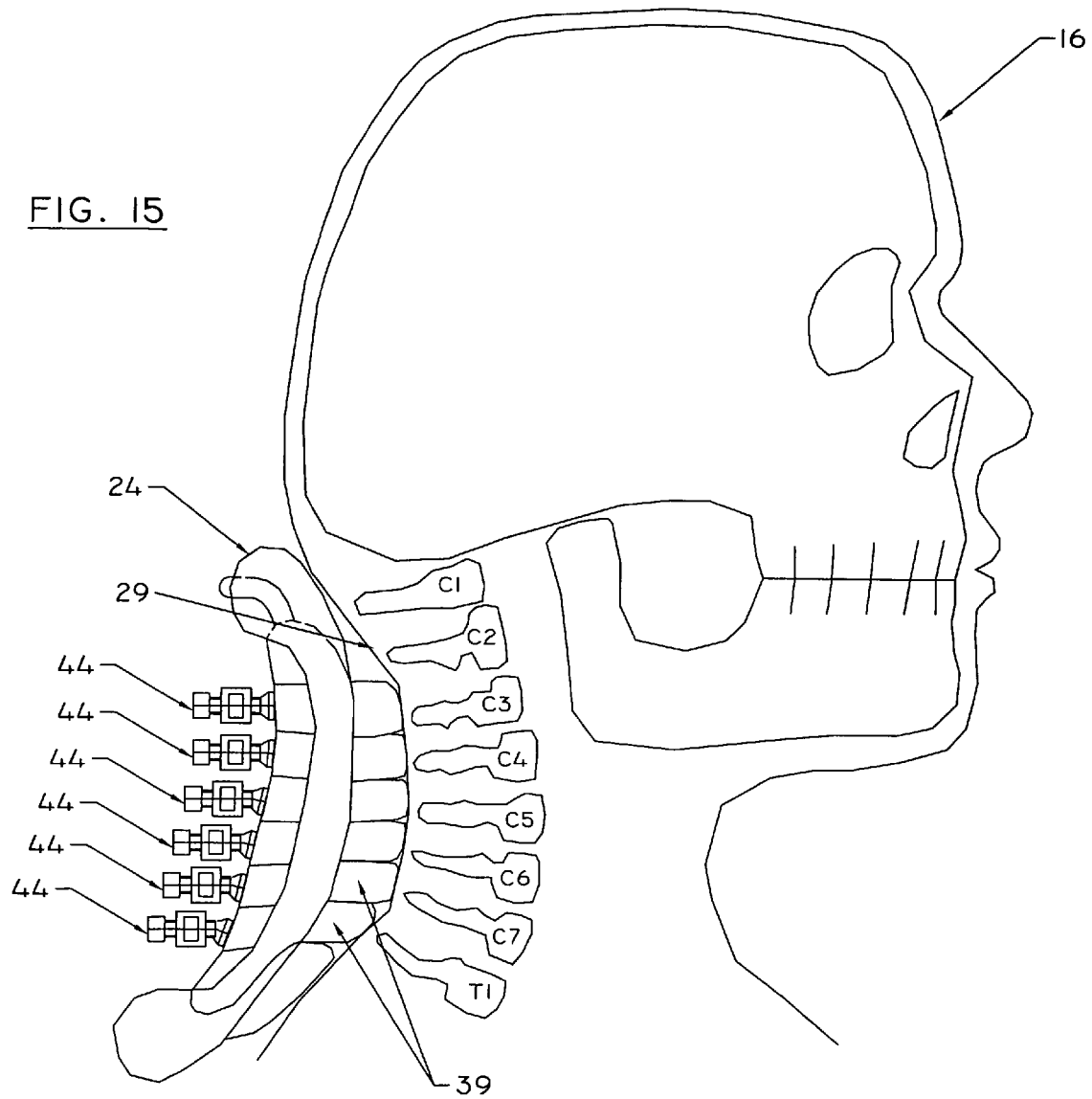
FIG. 15 is similar to FIG. 14 but individual tensioning means are shown which are inline with each individual foam lordosis pad.
Figure 16B:
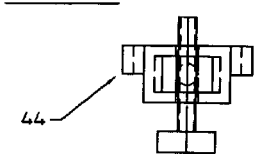
FIGS. 16A, 16B, and 16C show top, front and side schematic views of the tensioning mechanism used in FIGS. 14 and 15.
Figure 16A:
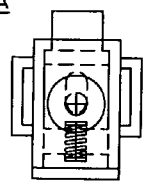
Figure 16C:
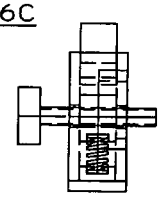
Figure 17:
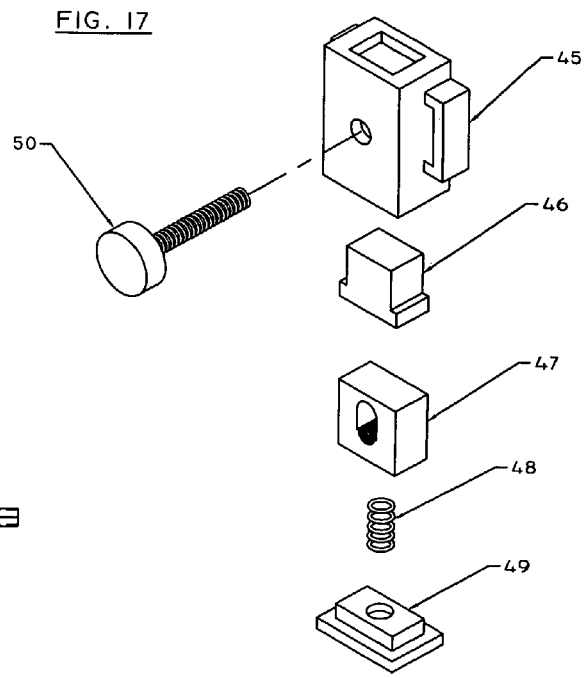
FIG. 17 is a schematic exploded view of the tensioning mechanism of FIGS. 16A, 16B and 16C.

As also mentioned, pads 39 can be non-inflatable units formed of rigid or soft foams or other materials. In such instances the pads can be selectively advanced against desired vertebrae by simple mechanical arrangements. The distal ends of the pads 39 (remote from the patient) can be covered by hard plates, which are biased toward the patient by an adjustable threaded member 50 extending through housing 45 to a point at the rear of the assembly. As shown in FIG. 14, a plurality of adjustable advancing means 44 are associated with individual foam pads 39. A suitable construction for means 44 is shown in FIGS. 16A, 16B, 16C and 17 The threaded member passes through a mating half nut 47 which is in contact with button 46 and retained by spring 48 and end cap 49 which bears against the assembly and which by its rotation can enable the adjustment.

Pads 39 can also be inflatable, but instead of directly bearing against the user's spine, can drive separate but contacting pads against the spine, where such separate pads are comprised of foams or other materials.

A key aspect of the present invention is that means are provided which interconnect the chin-mastoid piece to the shoulder collar assembly; such that these means are manually and incrementally adjustable so that the chin-mastoid piece may simultaneously be moved in two explicit directions, one of these being in an anterior/posterior direction, i.e. along the Z axis, and also in a vertical direction with respect to the shoulder collar assembly. Furthermore these two types of simultaneous movement are such that the displacement along the vertical direction is proportional to the incremental simultaneous displacement along the Z axis. The functioning of these principles of the invention are best appreciated by viewing FIG. 18 which very graphically illustrates (at top portion of the Figure) the changes in the configuration (at A, B, and C) of the head and spine and the changes in the spinal lordosis which occur as the foregoing step-wise and time-wise adjustments are effected (via knob 35) in the positioning of the chin-mastoid piece 12 relative to the shoulder collar assembly 14.

The present invention thus seeks to treat the medical condition now known as Cervical Kyphosis/Forward Head Posture Syndrome. In order to correct this crippling condition, the patient's neck curve must be supported at the precise vertebrae that are causing the reversal of the neck curve while simultaneously repositioning the head rearward to align over the shoulders. This latter movement is a rearward translational movement and not the rotational movement as can be seen in the cited prior art.

Figure 18:
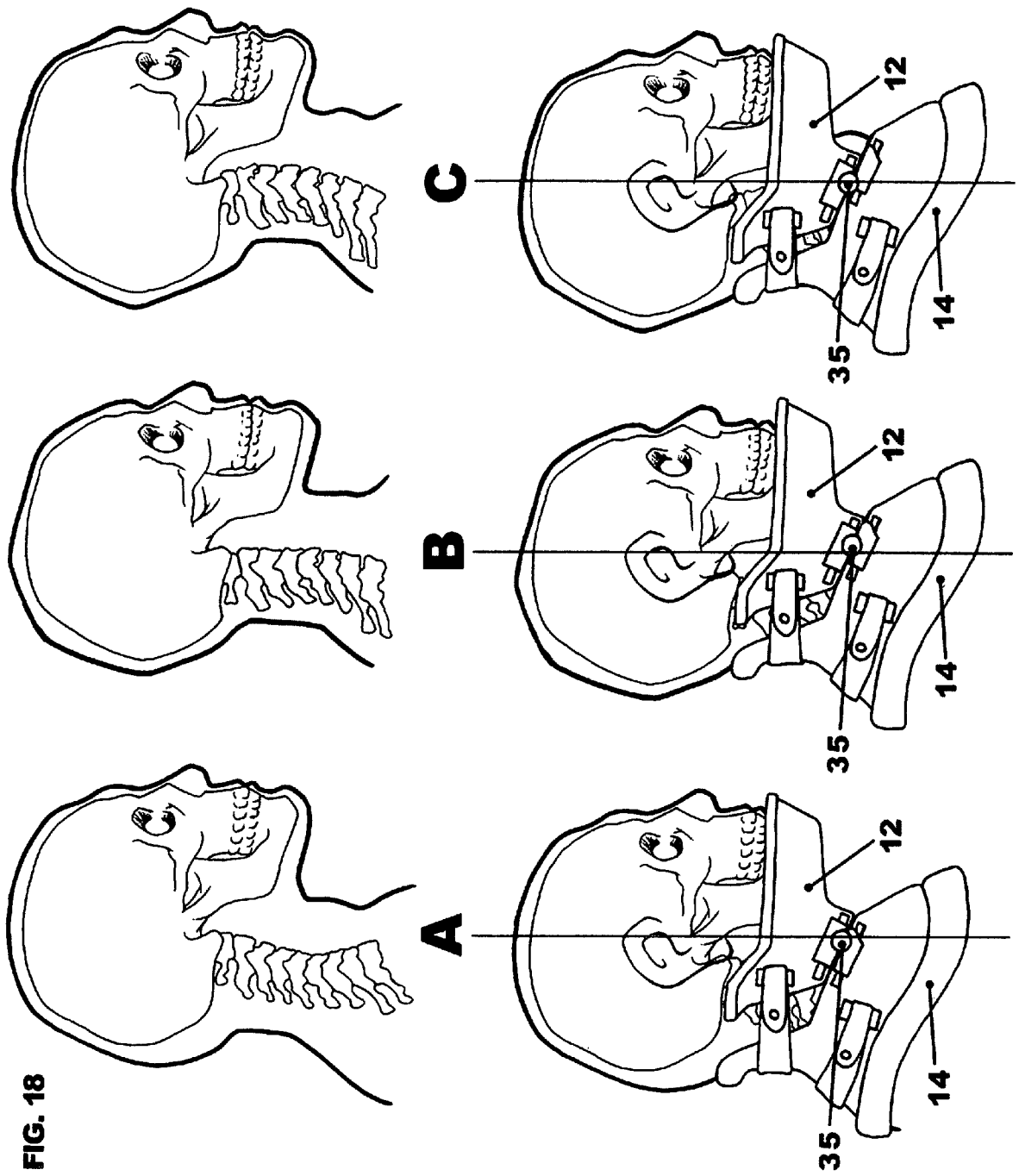
FIG. 18 is a schematic cross-sectional view depicting the sequential changes that occur in the patient's head position and spinal configuration as successive step and time-wise incremental adjustments are carried out by means of the present invention.

The progressive improvement of the cervical lordosis requires precise support to the offending misaligned vertebrae. In the examples cited, the vertebra is C5. The progressive postural movement the present invention produces, is shown in FIG. 18. Typically as treatment progresses from A to B in approximately one month, B shows the head moved in the −Z direction to align over the shoulders. There is no extension or flexion movement required. The neck in B moves in a +Z or forward direction. A full contoured support would not be sufficient because it spreads the support over a large area, C1-C7. Finally, in FIG. 18 at C, the neck curve has been restored to normal and the forward head posture has been repositioned over the shoulders by the collar's upward angled −Z directional movement. These motions and intended clinical correction of Forward Head Posture and Cervical Kyphosis are not discussed in the cited prior art and could not be achieved by the cited prior art because there must be simultaneous correction of both forward head posture and a precise support to the misaligned cervical vertebrae in order to change the cervical kyphosis into a cervical lordosis. This treatment will prevent cervical arthritis and cervical disc degeneration and painful neck misaligmnents.

While the present invention has been set forth in terms of specific embodiments thereof, the instant disclosure is such that numerous variations upon the invention are now enabled to those skilled in the art, which variations yet reside within the scope of the present teaching.

For example, since the FHP is a position that produces damaging structural stress on the entire spine it is reasonable to apply the collar in post-operative spine surgery patients. This would apply to cervical, thoracic, or lumbo-pelvic post surgical procedures. This would allow healing of the spinal joints without the damaging shear and moment mechanical stresses produced by the forward head posture position. For the above reasons the collar could also be used in post traumatic situations from car accidents or sports injuries, etc. Therefore hospitals and EMT personnel would desirably employ its use. The lordosis correction assembly can also be used with conventional cervical collars where forward head posture correction would be difficult, i.e., with older patients where fusion of spinal joints has advanced to a point where minimal movement is possible. These conditions would still benefit from some mild lordosis support. This would reduce some of the mechanical strain and pain in these patients.

Accordingly, the invention is to be broadly construed and limited only by the scope and spirit of the claims now appended hereto.

The invention claimed is:

1. A forward head position correction collar comprising in combination:
   a) a shoulder collar assembly;
   b) a chin-mastoid piece for engaging and positioning the head of a wearer of the collar;
   c) means interconnecting said chin-mastoid piece to said shoulder collar assembly for manually and incrementally adjusting said chin-mastoid piece with respect to said shoulder collar assembly in an anterior/posterior (Z-axis) direction along the Z-axis; and said means further interconnecting said chin-mastoid piece to said shoulder collar assembly to displace said chin mastoid piece in a vertical direction with respect to said shoulder collar assembly simultaneously with and proportional to the incremental adjustment of said chin piece along said Z-axis ; the said vertical displacement of said chin-mastoid piece with respect to said shoulder assembly and which is proportional to the Z-axis displacement for said chin support piece being that yielded by a point moving at a 5-25 degree slope with respect to the Z-axis; said means interconnecting said chin-mastoid piece to said shoulder collar assembly comprising a track affixed to said chin mastoid piece which is disposed at a slope having a vertical to horizontal rate of change corresponding to the said vertical and horizontal displacement of said chin mastoid piece with respect to said shoulder assembly and a pinion gear engaged with teeth in said track, and means for displacing said chin mastoid piece with respect to said shoulder assembly in accordance with the rotational position of said pinion gear; whereby to adjust the supported head of the wearer from the forward head position to an increasingly corrected position; and
   d) further including a lordosis correction assembly secured to the rear of said collar and engageable with the rear of the wearer for applying corrective forces by enabling increased pressure to be brought against specified vertebrae; said assembly comprising a plurality of separate, adjoining units, each having an advanceable surface which can be individually advanced against a selected of said vertebrae from the posterior of the vertabrae.

2. A forward head position correction collar in accordance with claim 1, wherein the said vertical displacement of said chin-mastoid piece with respect to said shoulder assembly and which is proportional to the Z-axis displacement for said chin support piece is that yielded by a point moving at a 10-25 degree slope with respect to the Z-axis.

3. A forward head position correction collar in accordance with claim 2, wherein the advanceable surfaces of said units of said corrective assembly are defined by a plurality of separate side by side pads.

4. A forward head position correction collar in accordance with claim 3, wherein the distal ends of said pads are selectively displaceable toward the wearer's vertebrae to enable selective increase of pressure against selected vertebrae.

5. A forward head position correction collar in accordance with claim 4, wherein said pads are individually inflatable to enable said displacement.

6. A forward head position correction collar in accordance with claim 2, further including means for locking the position between said chin mastoid piece and said shoulder assembly when the desired adjustment has been attained.

7. A forward head position correction collar in accordance with claim 6, wherein said locking means is releasable for enabling further adjustment.

8. A forward head position correction collar in accordance with claim 2, including said track and pinion gear at each lateral side of said correction collar, to enable balanced displacement at each lateral side of the collar.

9. A forward head position correction collar in accordance with claim 2, wherein said corrective assembly comprises an inflatable chamber and a surface facing the user which corresponds in shape to the desired corrections.

10. A forward head position correction collar in accordance with claim 2, wherein said lordosis correction assembly secured to the rear of said collar is engageable with the rear of the wearer for applying corrective forces to the upper, middle and/or lower cervical spine.

11. A forward head position correction collar in accordance with claim 2, wherein said lordosis correction assembly secured to the rear of said collar is engageable with the rear of the wearer for applying corrective forces to at least the cervical vertebrae of said wearer.

12. A forward head position correction collar in accordance with claim 2, wherein the said vertical displacement of said chin-mastoid piece with respect to said shoulder assembly and which is proportional to the Z-axis displacement for said chin support piece is that yielded by a point moving at about a 10 degree slope with respect to the Z-axis.

* * * * *